United States Patent [19]

Moubayed et al.

[11] Patent Number: 5,683,233

[45] Date of Patent: Nov. 4, 1997

[54] NON-ROLLING TYPE PERISTALTIC PUMP HAVING PRESSURE PLATE MOUNTED TUBE BIASING MEANS

[76] Inventors: Ahmad-Maher Moubayed, 22212 Destello, Mission Viejo, Calif. 92691; Rogelio Blanco Jester, Lago Tanganica 716, Jardines Del Lago, Mexicali, B.C., Mexico

[21] Appl. No.: 731,777

[22] Filed: Oct. 18, 1996

[51] Int. Cl.$^6$ ............................................ F04B 43/12
[52] U.S. Cl. .................................................... 417/474
[58] Field of Search ............................ 417/474, 477.9, 417/478; 604/153

[56] References Cited

U.S. PATENT DOCUMENTS

| 2,861,652 | 11/1958 | Small | 417/478 |
| 4,648,812 | 3/1987 | Kobayashi et al. | 417/474 |
| 4,671,792 | 6/1987 | Borsanyi | 417/474 |
| 4,893,991 | 1/1990 | Heminway et al. | 417/474 |
| 5,575,631 | 11/1996 | Jester et al. | 417/474 |

FOREIGN PATENT DOCUMENTS

| 3202251 | 8/1983 | Germany | 417/474 |
| 1366693 | 1/1988 | U.S.S.R. | 417/474 |

Primary Examiner—Roland McAndrews
Attorney, Agent, or Firm—John R. Duncan; Frank D. Gilliam

[57] ABSTRACT

A peristaltic pump for pumping liquids through a resilient tube. The pump includes a platen against which a resilient tube is placed. A cam assembly is positioned adjacent to the platen and tube. A plurality of pump fingers are mounted between tube and cam assembly in a manner permitting movement of the pump fingers toward and away from the tube. As the cam assembly rotates, the fingers are pressed toward the tube sequentially so as to pump liquid through the tube. The pump finger ends should press the tube sufficiently to at least nearly occlude the tube and prevent back flow without over pressing and damaging the tube. A transverse pinch finger is provided in a cavity in the platen opposite each pump finger, with a tip on each finger spring biased to extend from the tube pressing face of the platen. At the tube occluding position, the pump finger nearly occludes the tube and the pinch finger completes occlusion without pressing the tube beyond the fully occluded position.

16 Claims, 2 Drawing Sheets

NON-ROLLING TYPE PERISTALTIC PUMP HAVING PRESSURE PLATE MOUNTED TUBE BIASING MEANS

BACKGROUND OF THE INVENTION

This invention relates in general to fluid pumps and more specifically to a peristaltic pump having cam driven plurality of fingers for sequentially engaging a resilient tube to create liquid flow through the tube and a plurality of pinch fingers mounted in a platen to cooperate with the fingers.

Conventional linear and rotary peristaltic pumps typically have a section of resilient tubing positioned between a wall and a set of rollers or reciprocating pushers that progressively compress sections of the tubing to pump liquids. Such pumps are often used in medical applications, such as intravenous infusion or withdrawing fluids such as in a wound drainage system. These pumps operate in a positive manner and are capable of generating substantial outlet pressures.

Typical linear peristaltic pumps include those described by Sorg et al. in U.S. Pat. No. 2,877,714, Borsannyi in U.S. Pat. No. 4,671,792, Heminway et al. in U.S. Pat. No. 4,893,991 and Canon in U.S. Pat. No. 4,728,265. While generally effective, these pumps are large, complex and cumbersome, requiring a drive shaft parallel to a resilient tube and a plurality of cams along the drive shaft to move pushers toward and away from the tube.

Rotary peristaltic pumps generally dispose a resilient tube along a circular path, with a number of rollers mounted around the circumference of a circular rotor sequentially rolling along the tube to occlude the tube and force liquid through the tube. Typical of such pumps are those disclosed by Soderquist et al. in U.S. Pat. No. 4,886,431 and Kling in U.S. Pat. No. 3,172,367. These pumps often have relatively low efficiency and impose high shear and tension stresses on the tube causing internal tube wall erosion or spallation. The tube may eventually be permanently deformed so that the tube becomes flattened into a more oval shape and carries less liquid.

Another type of peristaltic pump has a tube arranged along a circular path with a cam member within the circle sequentially moving a plurality of blunt pushers or fingers outwardly to sequentially compress the tube from one end of the path to the other. Typical of these pumps are those shown by Gonner in German Patent No. 2,152,352 and Tubospir in Italian Patent No. 582,797.

In both types of pumps the pressure imposed by the blunt fingers reduces tube life, sometimes causing internal tube wall erosion or spallation, which results in particulate matter getting into the fluid stream. Tube with different wall thicknesses cannot be accommodated by these pumps, since with thinner than standard tubes the fingers will not properly occlude the tube and with thicker than standard tubes the tube will close prematurely and be subject to excessive compression, requiring higher cam drive power and causing excessive wear on the cam and tube.

Thus, there is a continuing need for peristaltic pumps of greater simplicity, small size, low drive power requirements and which can accommodate resilient tubes of varying wall thickness while reducing wear and internal erosion of the resilient tube.

SUMMARY OF THE INVENTION

The above-noted problems, and others, are overcome in accordance with this invention by a peristaltic pump having a platen for supporting a resilient tube, a multi-lobe cam or cam assembly rotatable adjacent to the platen, a plurality of pump fingers riding on the cam as cam followers and guided to move in a direction toward and away from said platen and a plurality of pinch fingers at the platen surface opposite each pump finger to complete occlusion of the tube without appreciably damaging the tube.

Each pump finger has a face for engaging a tube placed on said platen. Further, each pump finger includes a roller between the body of the pump finger and the cam to ride on the cam in the manner of a roller bearing, reducing wear.

The platen includes a pinch finger opposite each pump finger and lying transverse to the tube. Each pinch finger has a narrow tip or ridge that can extend above the platen surface to engage the tube when the pump finger presses against the opposite tube surface. In one embodiment, the pinch fingers may be made as part of the platen surface or may be fastened thereto. Since these narrow ridges only engage the tube along a narrow line, they can press into the tube without appreciably damaging the tube, as would occur if the tube were pressed between the platen itself and the relatively broad end of a pump finger. Thus, if the tube wall is thicker than normal, the tip simply presses deeper into the tube during tube occlusion.

In a particularly preferred embodiment, which can accommodate a greater range of tube wall thicknesses and which substantially eliminates damage to the tube, the pinch finger tip is elastically biased against the tube and can retract where the tube wall is oversize. A pinch finger is located in a slot in the platen opposite each pump finger. Each pinch finger includes biasing means, such as a spring or a resilient pad, to press an elongated, transverse, pinch finger tip outwardly of the slot and into engagement with the tube. When the cam means causes a pump finger to extend the maximum distance toward the tube, the tube normally is not quite occluded. The biasing means engaging each pinch finger presses the tip outwardly to squeeze the tube between each pair of opposing pinch finger and pump finger, fully occluding the tube without significantly penetrating or crushing the tube wall.

Where the tube wall thickness is slightly oversize, the pump finger may fully occlude the tube, so that the pinch finger tip extends only a short distance or even remains coplanar with the platen surface. If the tube wall thickness is slightly undersize, the tip will simply extend a greater distance beyond the platen surface to fully occlude the tube. Thus, the pinch finger will assure full occlusion even with undersized tubes without danger of damage to oversize tubes.

When the cam system is rotated, the pump finger engaging the highest area on the cam (widest lobe) or engaging the cam of a set that extends the furthest in the direction of rotation will be moved outwardly to squeeze the tube against the platen. As the cam system continues to rotate, the second pump finger will begin to squeeze the tube as the pinch finger on the first pump finger occludes the tube, to force liquid in the tube to flow in the same direction as the cam system rotates. As cam rotation continues, the subsequent fingers will sequentially squeeze the tube to push liquid and then occlude the tube. At the same time, the pump finger just behind the lobe will move away from the tube, allowing the tube to expand and fill with liquid. This sequence continues as cam system rotation proceeds.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
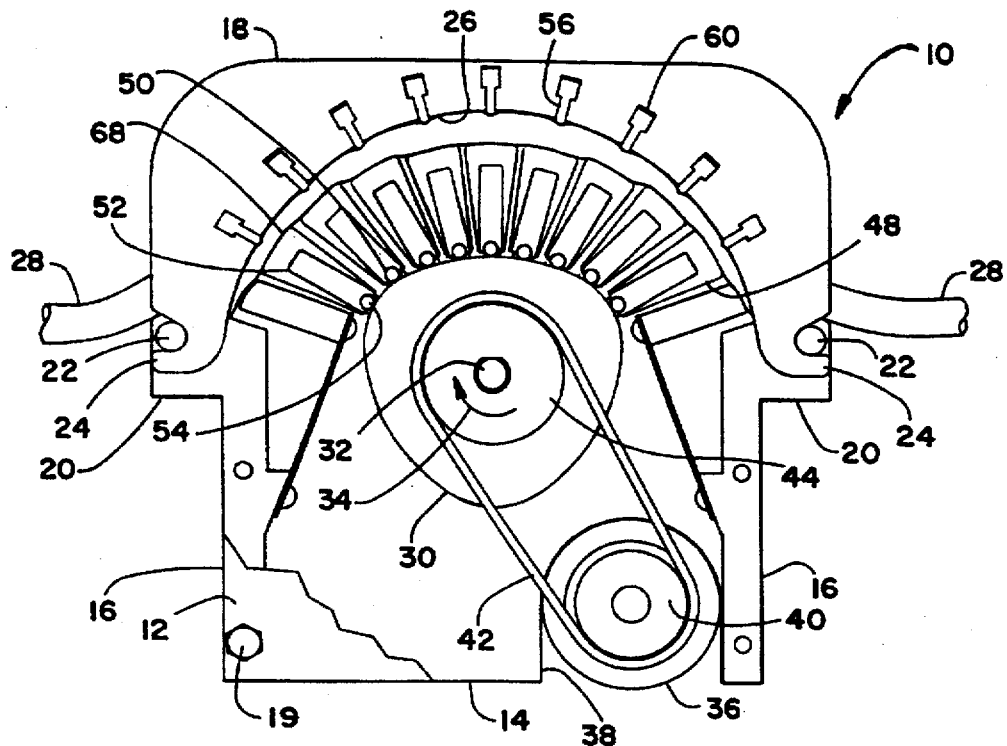
FIG. 1 is a side elevation view of a curvilinear pump having platen mounted pinch fingers.

Referring to FIG. 1, there is seen a curvilinear peristaltic pump 10 having a casing basically consisting of a back plate 14 (and corresponding front plate 12) and spacers 16. The casing is held together by a plurality of bolts 19 for ease of assembly and disassembly as needed. A removable cover 18 is secured to casing 10. Each spacer 16 includes a block 20 having a hole therethrough cooperating with a pin or bolt 22 and hook-shaped cover extensions 24 to hold cover 18 in place.

Cover 18 includes a concave curvilinear platen 26. While platen 26 may have any suitable surface, generally a cylindrical surface is preferred. A resilient tube 28 may be laid along platen 26, exiting through the open space between each pair of extensions 24.

A multi-lobed cam 30 is mounted for rotation about an axle 32 that extends through suitable bearings in front and back plates 12 and 14. Cam 30 may have any suitable number of lobes, two or more. For optimum performance with smallest size, the three-lobe cam shown is preferred. Where platen 26 is cylindrical, axle 32 is preferably at the axis of the platen. Cam 30 can be rotated in either direction to pump liquid through tube 28 in either direction. For convenience of operation explanation, cam 30 will be considered to be rotating clockwise, as indicated by arrow 34. Any suitable drive means may be used to rotate cam 30. In the preferred embodiment shown, an electric drive motor 36 extends through opening 38 in back plate 14 and is mounted on the back surface of front plate 12. Motor 36 has a drive shaft extending through front plate 12 to a pulley 40. A drive belt 42 extends from pulley 40 to pulley 44 mounted on cam axle 32. Pulleys 40 and 44 are sized to provide the desired cam rotation speed. A variable speed motor 36 may be used to allow cam rotation speed to be easily varied. If desired, a gear system could be used in place of belt 42, or a different drive system could be used, such as a conventional hydraulic drive, in place of the electric motor and belt drive system shown.

A plurality of pump fingers 48 are mounted for radial movement on front plate 12 and back plate 14 between cam 30 and platen 26. Any suitable number of pump fingers 48 may be used. Where a greater number of cam lobes are used, fewer fingers will generally be used. On the other hand, if narrow fingers 48 are used, a larger number may be provided. A large scale pump will generally use a larger number of fingers. A preferred number of pump fingers 48 for a three-lobe cam 30 of maximum efficiency coupled with small size is from 7 to 11 pump fingers, with 9 generally being optimum.

Preferably, a plurality of opposed radial grooves (not seen) are provided in back plate 14 and a corresponding front plate to receive side ridges 52 that extend into the corresponding grooves. The extension and ridge arrangement allows the pump fingers 48 to slide radially toward and away from axis 32 as the cam lobes gradually extend and retract against the pump fingers.

Each pump finger 48 includes a transverse cylindrical recess at a first end 50 for rotatably receiving a bearing roller 54. Rollers 54 freely roll on the surface of cam 30 in the manner of roller bearings, reducing wear on the cam surface.

Figure 3:
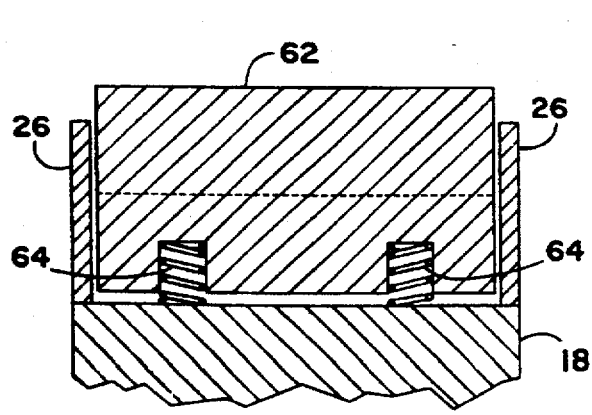
FIG. 3 is a section view, taken on line 3—3 in FIG. 2.
Figure 2:
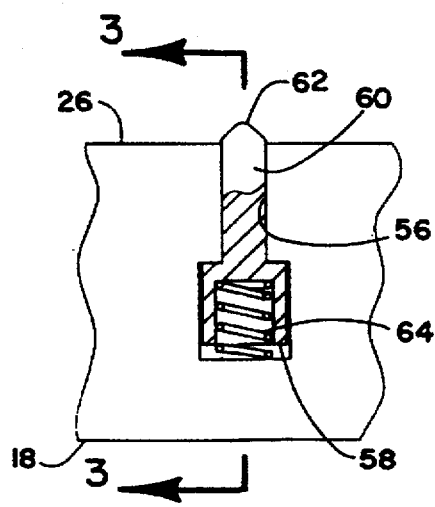
FIG. 2 is a detail side elevation view, partially cut away, of the pinch finger assembly having a spring biased pinch finger.

As detailed in FIGS. 2 and 3, a transverse, "T" shaped slot 56 is formed across cover 18 with the slot leg extending from platen 26. A base 58 fits within the crosspiece of "T" slot 56. A transverse pinch finger 60 extends from base 58 and fits with in the leg portion of "T" slot 56 and has a tip 62 extending out of the slot to extend above the platen surface. One or more springs 64 (preferably two, as seen in FIG. 3) bias base 58 and tip 62 of pinch finger 60 toward the extended position.

The pump operates in the following manner. As seen in FIG. 1, two lobes of cam 30 are located at the beginning and end of the series of pump fingers 48. At this position, pump fingers 48 engaging the central portion of tube 28 along the middle of platen 26 are relatively withdrawn and those at the ends are relatively extended, thereby creating a zone of occlusion. Thus, the central portion of tube 28 is filled with liquid and the ends are substantially occluded. As cam 30 rotates in the direction of arrow 34, the second left pump finger 48 is pressed further against tube 28 while the rightmost pump finger begins to withdraw. Liquid is thus pushed in a zone of occlusion toward the right or outlet end of tube 28 and begins to exit. As cam rotation continues, pump fingers 48 are sequentially extended from the left and withdrawn at the right, forcing liquid in tube 28 toward the outlet end.

As seen in the central region of tube 28 in FIG. 1, pinch fingers 60 under the forces of springs 64 are relatively extended. The leftmost pinch finger 60 is slightly extended, but second end 68 of pump finger 48 has not entirely occluded tube 28. Pinch finger 60 is extended sufficiently, under the force of spring 64, opposite pump finger 48 to occlude the tube. With a thin wall tube 28, tip 62 of pinch finger 60 will extend further to occlude the tube. With a thick walled tube, tip 62 of pinch finger 60 will only extend a shorter distance until the tube is occluded. Thus, only enough force is applied through the pinch finger to occlude the tube.

In prior art pumps, the pumping finger extended only a single preset distance under the strong mechanical force of a cam. With those arrangements, thin tubes are not entirely occluded and thick walled tubes are crushed beyond closure, often resulting in rapid wear, internal wall erosion and spallation with the resulting injection of particles of wall material into the liquid stream, of great concern in many infusion operations. Only a short degree of extension and retraction of pinch fingers 60 is required to produce this highly advantageous result, typically from about 0.2 to 1.0 mm.

Figure 4:
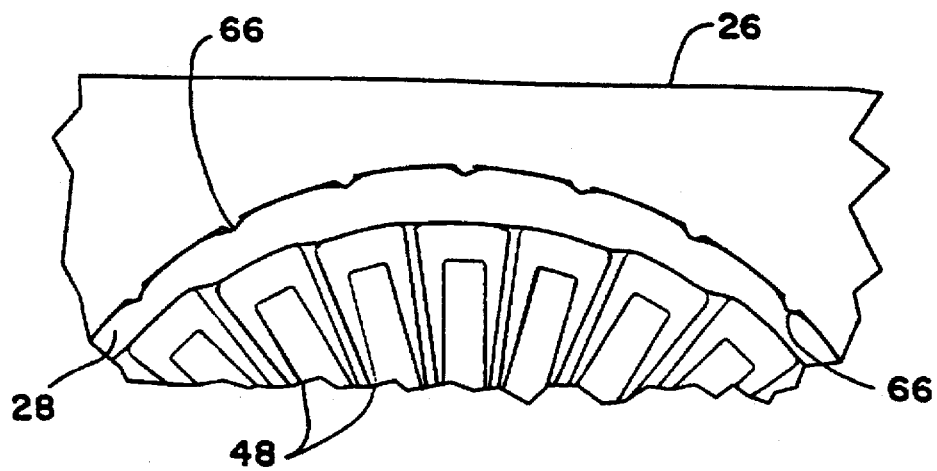
FIG. 4 is a detail side elevation view of a fixed pinch finger tip.
Figure 5:
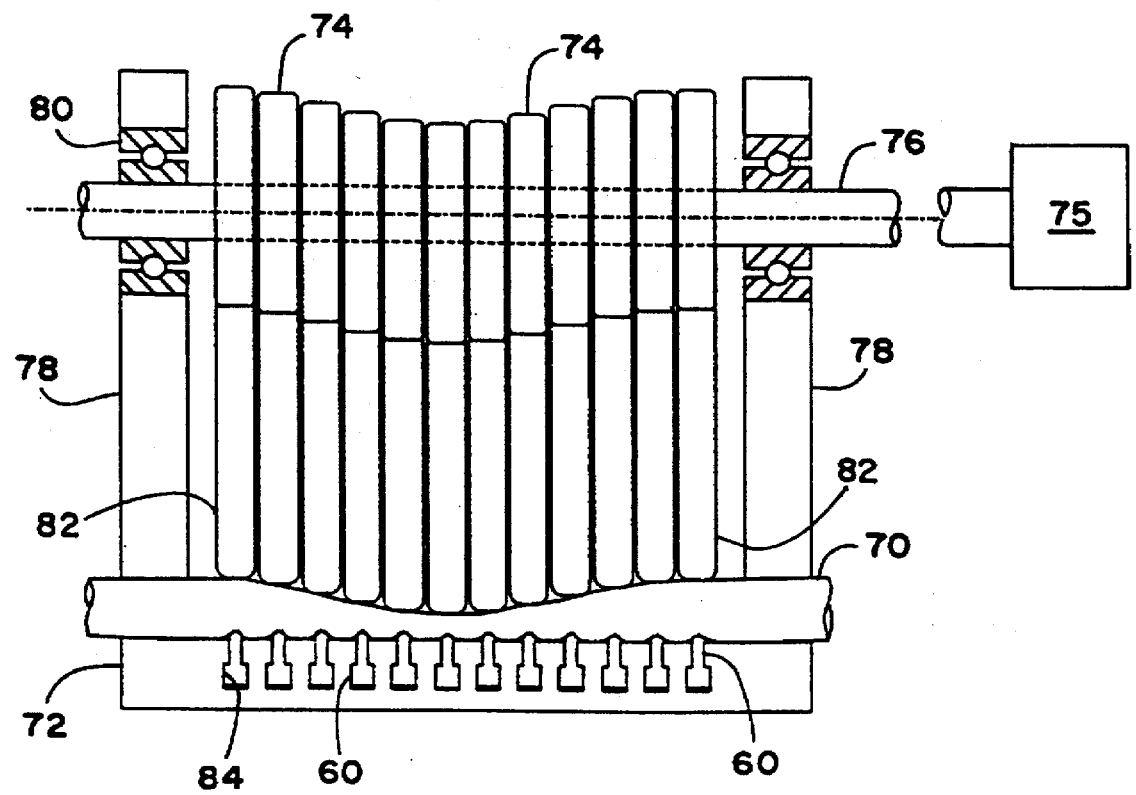
FIG. 5 is a side elevation view of a linear peristaltic pump with platen mounted pinch fingers.

FIG. 4 shows an alternative embodiment of the platen mounted pinch fingers that is useful with either the curvilinear platen of FIG. 1 or the flat platen of FIG. 5. Here, the pinch fingers are in the form of transverse tips or ridges 66 formed across the surface of platen 26 transverse to tube 28.

Pump fingers 48 are set such that when a pump finger is moved to the full distance toward tube 28, the pinch finger tips 66 will penetrate slightly more than would be required for full occlusion. Then, an undersized tube will still be fully occluded and an oversize tube will be penetrated by tips 66 to a slightly greater extent. Due to the small area and rounded ends on tips 66, significant damage to tube 28 is unlikely.

Tips 66 can be formed during manufacturing of platen 28 by conventional manufacturing methods, or may be secured as individual strips to the platen surface by welding, adhesive bonding, etc. While the embodiment of FIG. 4 is simple and inexpensive to manufacture and generally very effective, for optimum tube life the embodiment of FIGS. 2 and 3 is preferred.

FIG. 5 shows another pump embodiment in which the platen mounted pinch finger system of the invention can be used. Here,, a tube 70 rests on a flat platen 72. A set of cams 74 is mounted on an axle 76 arranged parallel to platen 72. Axle 76 is mounted on a uprights 78 through bearings 80. Axle 76 may be rotated by any suitable drive means, such as an electric motor (not shown). The cam assembly 74, drive, etc. are all conventional in the art. Typically each cam may be in the form of an off-center circle, ellipse, etc.

A pump finger 82 is mounted in a conventional support, allowing vertical movement relative to platen 72. As axle 76 is rotated, cams 74 progressively push pump fingers 82 down against tube 70 from one end toward the other, forcing liquid in tube 70 to move in that direction. As explained above, the occluding distance between each pump finger 82 and platen 72 is fixed so that a tube of precise predetermined wall thickness will be just barely fully occluded. If the walls of tube 70 are greater than normal, the tube will be crushed and damaged. If the tube walls are thinner than normal, full occlusion will not occur and back flow through the pump will occur, so that the expected pumping rate will not be achieved.

A plurality of pinch fingers 60 of the sort detailed in FIGS. 2 and 3 are arranged in slots 84 in platen 70, arranged transverse to tube 70. Of course, the pinch tip embodiment of FIG. 4 may also be used. As described above, with a normal tube, the tips of pinch fingers 60 will be spring pressed toward tube 70 to extend slightly above the surface of platen 72 to fully occlude the tube. With a thinner walled tube, pinch fingers will be spring pressed to further extend above the platen surface, so that tube 70 is still occluded. Where the walls of tube 70 are oversize, the tips of pinch fingers 60 may only extend a shorter distance until the tube is occluded.

Thus, the platen mounted pinch fingers in both the embodiments of FIGS. 1 and 5 will accommodate a range of tube sizes without either damaging the tube or degrading pump performance.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. A peristaltic pump which comprises:

a platen;

a rotatable cam means spaced from said platen;

means for rotating said cam means in a first direction;

a plurality of pump fingers, each having a first end riding on a cam surface of said cam means and a second end adjacent to said platen;

said cam surface configured to first sequentially move said pump fingers toward said platen and second sequentially allow said pump fingers to move away from said platen;

a pinch finger tip mounted on said platen opposite each of said pump fingers, each tip extending above the surface of said platen transverse to a tube in place on said platen;

each of said pinch finger tips being mounted on a pinch finger slidably mounted in a sloe in said platen opposite each said pump finger;

each of said pinch finger tips being extendable out of said slot a predetermined maximum distance toward said opposite pump finger;

whereby a resilient tube may be interposed between said platen and said second pump finger ends so that as said pump fingers are sequentially moved toward said platen, liquid in said tube will be pumped in said first cam rotation direction and each pinch finger will occlude said tube when each said pump finger reaches a position closest to said platen.

2. The peristaltic pump according to claim 1 wherein each of said tips is a fixed ridge on the surface of said platen.

3. The peristaltic pump according to claim 1 wherein said platen is flat and said cam assembly comprises a plurality of parallel cams mounted on an axis for rotation therewith.

4. The peristaltic pump according to claim 1 wherein said platen surface is cylindrical and said cam is rotatable around an axis concentric with said cylindrical platen surface.

5. The peristaltic pump according to claim 4 further including releasable latch means for attaching said platen to a cam support casing.

6. The peristaltic pump according to claim 4 wherein said cam is supported for rotation between parallel front and back plates.

7. A peristaltic pump which comprises:

a curved platen;

a rotatable multi-lobed cam spaced from said platen;

means for rotating said cam in a first direction;

a plurality of pump fingers, each having a first end riding on said cam and a second end adjacent to said platen;

means for interposing a resilient tube between said platen and said pump fingers;

said cam configured to first sequentially move said pump fingers toward said platen to compress said tube and second sequentially allow said pump fingers to be moved away from said platen;

each of said pump fingers sized to compress said tube as said cam moves said pump fingers toward said platen;

a plurality of pinch fingers mounted on said platen, each pinch finger oriented opposite one of said pump fingers so that said pump fingers and said pinch fingers engage opposite sides of said tube to fully occlude said tube; and each said pinch finger comprising a slidable member extending through a transverse slot in said platen and further including means for biasing each said pinch finger in a direction extending outwardly of said transverse slot.

8. The peristaltic pump according to claim 7 wherein each of said transverse platen slots extends into said platen and communicates with a cavity, said pinch finger slidably fitting within said slot and secured to a base in said cavity and further including at least one compression spring between said base and a wall of said cavity opposite said platen surface to bias said pinch finger outwardly of said transverse slot.

9. The peristaltic pump according to claim 7 wherein each said pinch finger is a transverse ridge on said platen opposite each pump finger.

10. The peristaltic pump according to claim 7 wherein said cam has at least two spaced lobes and cam diameter changes diameter from widest at said lobes to narrower between said lobes.

11. The peristaltic pump according to claim 7 wherein each pump finger carries a rotatable roller at said first end to engage and roll along said cam.

12. The peristaltic pump according to claim 7 further including releasable latch means for attaching said platen to a cam support casing.

13. The peristaltic pump according to claim 7 wherein said platen surface is cylindrical and said cam is rotatable around an axis concentric with said cylindrical platen surface.

14. A peristaltic pump which comprises:

a substantially flat platen;

a cam assembly comprising a plurality of parallel cams spaced from said platen;

means for rotating said cam assembly in a first direction;

a plurality of pump fingers, each having a first end riding on one of said cams and a second end adjacent to said platen for movement toward and away from said platen during rotation of said cam assembly;

means for interposing a resilient tube between said platen and said pump fingers;

said cam assembly configured to first sequentially move said pump fingers toward said platen to compress said tube and second sequentially allow said pump fingers to be moved away from said platen;

each of said pump fingers sized to compress said tube as said cam moves said pump fingers forward said platen;

a plurality of pinch fingers, each pinch finger mounted on said platen opposite one of said pump fingers so that said pump fingers and said pinch fingers engage opposite sides of said tube to fully occlude said tube; and each said pinch finger comprises a slidable member extending through a transverse slot in said platen and further including means for biasing each said pinch finger in a direction extending outwardly of said transverse slot.

15. The peristaltic pump according no claim 14 wherein each of said transverse platen slots extends into said platen and communicates with a cavity, said pinch finger slidably fitting within said slot and secured to a base in said cavity and further including at least one compression spring between said base and a wall of said cavity opposite said platen surface to bias said pinch finger outwardly of said transverse slot.

16. The peristaltic pump according to claim 14 wherein each said pinch finger is a transverse ridge on said platen opposite each pump finger.

* * * * *